(12) United States Patent
Garukyan

(10) Patent No.: US 6,941,983 B2
(45) Date of Patent: Sep. 13, 2005

(54) SYRINGE GUIDE

(76) Inventor: Grigor Garukyan, 601 Hawthorne St. #5, Glendale, CA (US) 91204

( * ) Notice: Subject to any disclaimer, the term of this patent is extended or adjusted under 35 U.S.C. 154(b) by 125 days.

(21) Appl. No.: 10/755,286

(22) Filed: Jan. 12, 2004

(65) Prior Publication Data

US 2005/0039817 A1 Feb. 24, 2005

Related U.S. Application Data

(60) Provisional application No. 60/496,544, filed on Aug. 21, 2003.

(51) Int. Cl.$^7$ ................................................. B65B 1/04
(52) U.S. Cl. .................... 141/97; 141/365; 141/366; 141/370
(58) Field of Search ............................... 141/2, 18, 27, 141/97, 319, 329, 363, 369, 370, 383; 604/403, 407, 411–416

(56) References Cited

U.S. PATENT DOCUMENTS 3,610,241 A * 10/1971 LeMarie ..................... 604/407
5,247,972 A * 9/1993 Tetreault ..................... 141/27
5,894,870 A * 4/1999 Maxwell ..................... 141/27
6,364,866 B1 * 4/2002 Furr et al. ................. 604/414
6,439,276 B1 * 8/2002 Wood et al. ................. 141/97
6,581,648 B1 * 6/2003 Zolentroff et al. ............ 141/2

* cited by examiner

Primary Examiner—Timothy L. Maust

(57) ABSTRACT

A syringe guide for a syringe and vial is disclosed. The syringe guide serves as a guide for the needle to be inserted into the vial. The syringe guide can be made in different sizes, with different materials, and using different constructive ways. It consists of a pipe having a large diameter at one end and a small diameter at the opposite end. The vial and syringe are placed in the syringe guide according to their relative diameters. The diameter of the syringe guide can increase due to the slit running the entire length. A wall inside the syringe guide where the small and large diameters of the pipe meet supports the vial. When withdrawing medication while both the vial and the syringe are in the guide, one does not have to hold the vial. The syringe guide makes working with a needle safer, cleaner, and easier.

1 Claim, 4 Drawing Sheets

FIG.1 "SCALE 1/2"

SYRINGE GUIDE

CROSS-REFERENCE TO RELATED APPLICATIONS

This non-provisional application is related to the provisional application filed on Aug. 21, 2003, application Ser. No. 60/496,544.

STATEMENT REGUARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

The invention is technically related to the puncturing process when removing liquid medication from a vial using a syringe. It also analogically relates to the movement of the needle on a sewing machine during the first puncture, because the needle is guided.

BRIEF SUMMERY OF THE INVENTION

The Syringe Guide consists of a plastic pipe with a slit running the entire length. One end of the pipe has a greater diameter than the opposite end. A medication vial (head first) is placed at the end with the greater diameter and a syringe (needle end first) is placed in the end with the smaller diameter. The Syringe Guide helps minimize needle sticks and makes drawing medication from a vial faster and easier.

BRIEF DESCRIPTION OF THE SEVERAL VIEWS OF THE DRAWINGS

The invention will be described in more detail using references to the appended drawings.

DETAILED DESCRIPTION OF THE INVENTION

The Syringe guide is made of transparent plastic, more specifically from plastics used to manufacture medical devises that can be sterilized, using injection molding. Different dimensions of the Syringe Guide can be manufactured. Generally, the Syringe Guide has been designed for use in emergency rooms, hospitals, clinics, and homes (administration of insulin). The advantages of this invention are that it makes aspiration of medication from a vial faster, safer cleaner, and easier. For example, when puncturing the vial with a needle one does not have to aim, the guide ensures that the needle punctures the center of the vial. In addition, when puncturing the vial one does not have to take caution with finger sticks because the guide forms a protective barrier around the syringe and the vial. Moreover, when the needle is inside the vial one does not have to hold the vial, one can aspirate the medication holding the syringe and the syringe plunger. Furthermore, the Syringe Guide somewhat protects the needle against dust and airborne microbes by forming a barrier from the outside environment.

The following part will use the drawings to explain the invention in detail. The safety syringe FIG. 1-1 consists of a plastic pipe. The pipe has a small diameter at one end and a larger diameter at the opposite end. The end of the guide with the large diameter has a length that is shorter then the length of the vial 3. The end with the smaller diameter has a length smaller then the length of the syringe 4 not including the needle. The end with the larger diameter is shorter then the end with the small diameter. FIG. 2 shows the positions of the syringe, the vial, and the Syringe Guide when assembled.

Figure 1:
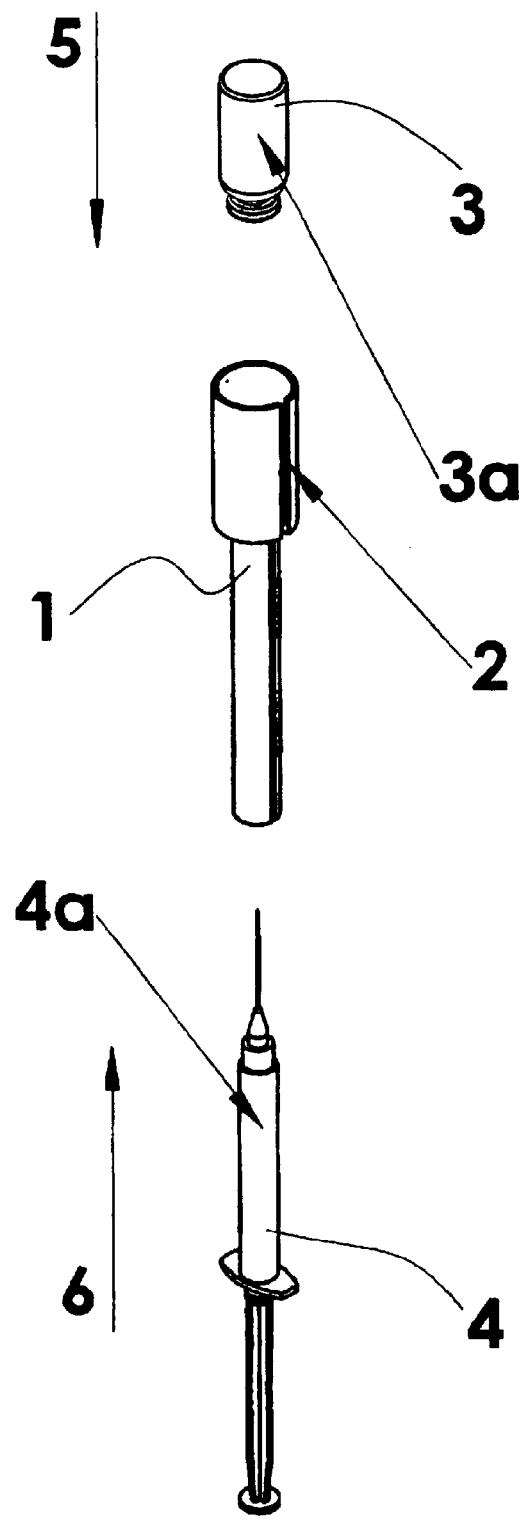
FIG. 1 depicts, an exploder assembly view of the Syringe Guide with the syringe and the vial.
Figure 2:
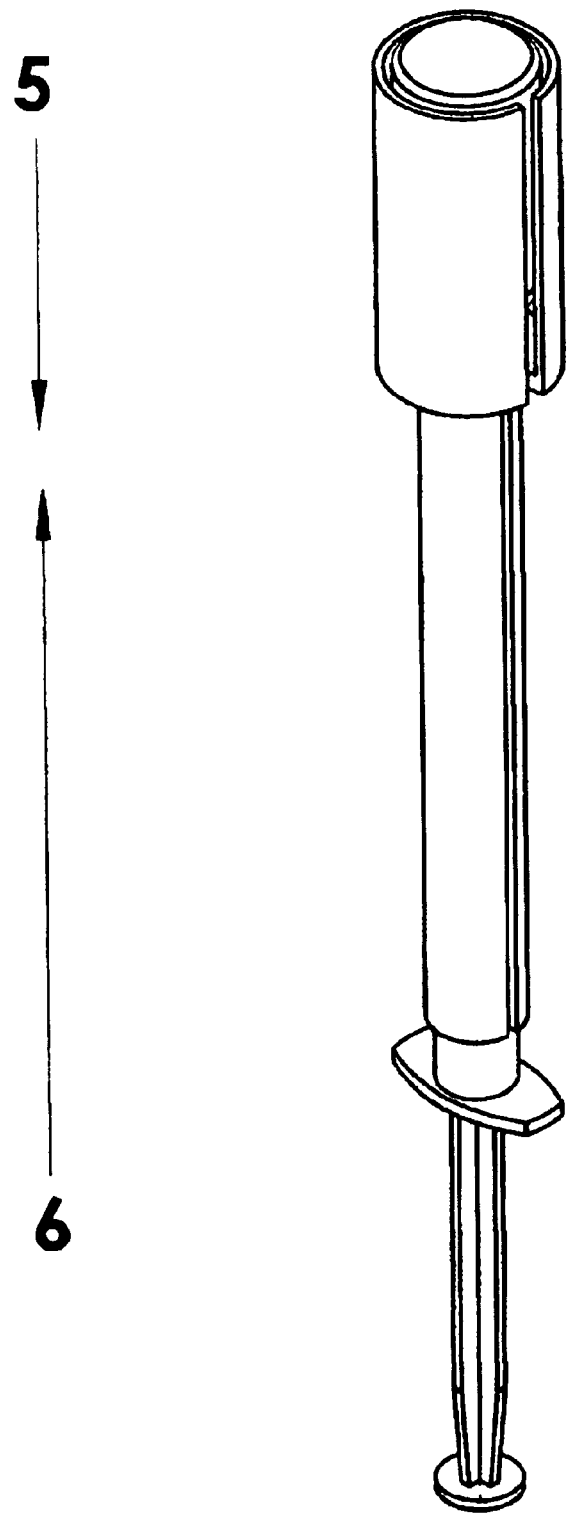
FIG. 2 depicts, an assembly view of the Syringe Guide with the syringe and the vial.

The end with the bigger diameter FIG. 1-1 has an internal diameter smaller then the external diameter of the vial 3. Also, the end with the smaller diameter has an internal diameter smaller then the external diameter of the syringe 4. This is done to ensure that when the syringe, Syringe Guide, and the vial are assembled FIG. 2 the Syringe Guide will expand its slit FIG. 1-2, and will grip the syringe and the vial.

Figure 3:
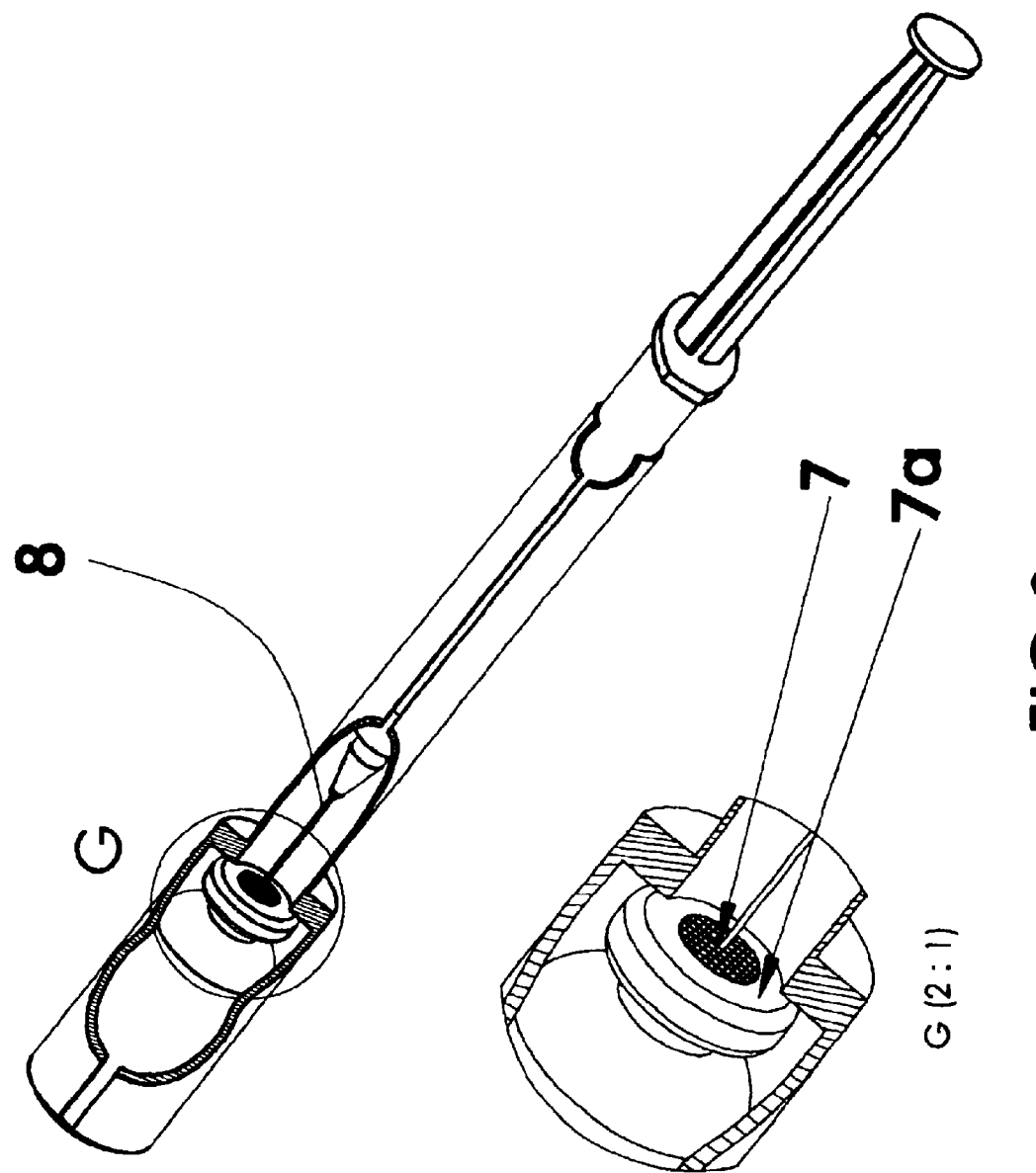
FIG. 3 depicts, an assembly view of the Syringe Guide with local sections and a magnified detail view of the puncturing area.
Figure 4:
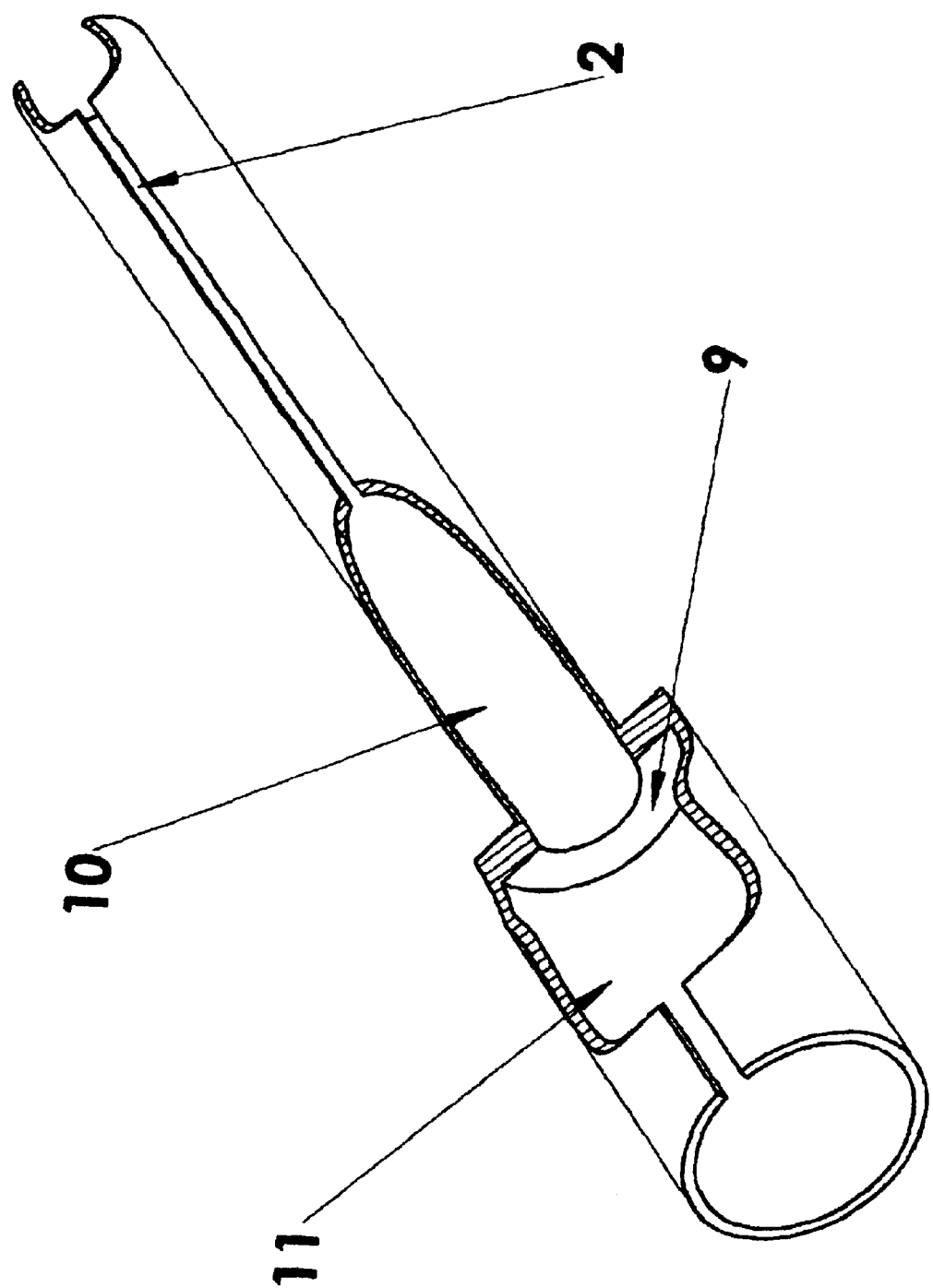
FIG. 4 depicts, the Syringe Guide and local sections.

The Syringe Guide is used in the following matter. After sanitizing the vial FIG. 1-3, the vial is inserted into the Syringe Guide FIG. 1-1 in the direction 5. Surface FIG. 1-3a comes into contact with surface FIG. 4-11 and the vial slides forward until surface FIG. 3 magnified view G-7a it comes into contact with FIG. 4-9 and stops. In order to insert the syringe in the Syringe Guide the Syringe Guide-vial assembly either has to be placed on a hard surface with the vial at the bottom or the assembly has to be held in one's hand with the vial being between the thumb and the index finger, followed by placing the thumb at the bottom of the vial to prevent the vial from slipping out. After uncapping the syringe FIG. 1-4 the syringe is placed in the Syringe Guide FIG. 1-1 in the direction 6. Surface FIG. 1-4a comes into contact with surface FIG. 4-10 the syringe FIG. 1-4 slides forward until the needle FIG. 3-8 punctures the center of the vial head FIG. 3 magnified view G-7 and the needle can be seen in the vial. During the puncturing process the Syringe Guide-vial assembly has to be in one of the two conditions as mentioned earlier to prevent the vial from slipping out of the Syringe Guide. After the puncturing process has occurred we have the Syringe Guide, vial and syringe assembly FIG. 2. To aspirate the medication from the vial, hold the assembly FIG. 2 so that the vial is pointing up. With one hand hold the syringe FIG. 1-4 and with the other hand hold the plunger of the syringe (no need to hold the vial) and aspirate. The syringe then can be removed by direction opposite FIG. 2-6, capped and ready for use. The vial can also be removed by direction opposite FIG. 2-5 and stored for later use.

I claim:

1. A syringe guide comprising: a transparent plastic pipe having first and second end portions, said first end portion being longer than said second end portion and adapted to hold a syringe, said second end portion having a larger diameter than said first end portion and adapted to hold a vial; and a continuous expandable slit running the length of said pipe in order to provide adjustability for various sized syringes and vials.

* * * * *